(12) United States Patent  
Ito

(10) Patent No.: US 7,471,762 B2  
(45) Date of Patent: Dec. 30, 2008

(54) TOTAL REFLECTION X-RAY FLUORESCENCE ANALYSIS METHOD

(75) Inventor: Shoko Ito, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 363 days.

(21) Appl. No.: 11/117,386

(22) Filed: Apr. 29, 2005

(65) Prior Publication Data

US 2005/0276378 A1 Dec. 15, 2005

(30) Foreign Application Priority Data

Jun. 15, 2004 (JP) ............................. 2004-177270

(51) Int. Cl.  
*G01N 23/223* (2006.01)

(52) U.S. Cl. .............................. 378/45; 378/44; 438/14

(58) Field of Classification Search .................. 378/44, 378/45, 46, 48, 49, 70, 76; 438/14  
See application file for complete search history.

(56) References Cited

U.S. PATENT DOCUMENTS

| | | | |
|---|---|---|---|
| 4,990,459 A | | 2/1991 | Maeda et al. |
| 5,220,591 A | * | 6/1993 | Ohsugi et al. ................ 378/45 |
| 5,249,216 A | * | 9/1993 | Ohsugi et al. ................ 378/46 |
| 5,395,446 A | * | 3/1995 | Kageyama et al. ........... 118/52 |
| 5,457,726 A | * | 10/1995 | Miyazaki ..................... 378/45 |
| 5,636,256 A | * | 6/1997 | Matumura et al. ........... 378/45 |
| 5,686,314 A | * | 11/1997 | Miyazaki ..................... 436/177 |
| 5,742,658 A | * | 4/1998 | Tiffin et al. ................... 378/44 |
| 5,754,620 A | * | 5/1998 | Hossain et al. ............... 378/45 |
| 5,994,142 A | | 11/1999 | Yamasaki et al. |
| 6,053,984 A | * | 4/2000 | Petvai et al. .................. 134/3 |
| 6,173,036 B1 | * | 1/2001 | Hossain et al. ............... 378/45 |
| 6,475,291 B1 | * | 11/2002 | Petvai et al. .................. 134/3 |
| 6,735,276 B2 | * | 5/2004 | Ikeshita et al. ............... 378/45 |
| 6,911,096 B2 | * | 6/2005 | Watanabe ..................... 134/10 |
| 6,939,410 B2 | * | 9/2005 | Ko et al. ........................ 134/3 |
| 6,960,265 B2 | * | 11/2005 | Heo et al. ...................... 134/3 |
| 2005/0048659 A1 | | 3/2005 | Shiramizu |

(Continued)

FOREIGN PATENT DOCUMENTS

DE 197 13 090 A1 11/1997

(Continued)

OTHER PUBLICATIONS

Shimazaki et al., "Analysis of Low Metallic Contamination on Silicon Wafer Surfaces by VPT-TXRF—Quantification of 109 atoms/cm2 Level Contamination—", 456-459, ISSM 2005.*

(Continued)

*Primary Examiner*—Allen C. Ho  
(74) *Attorney, Agent, or Firm*—Finnegan, Henderson, Farabow, Garrett & Dunner, L.L.P.

(57) ABSTRACT

A semiconductor substrate is exposed to an acid vapor, an impurity on the surface of the semiconductor substrate exposed to the acid vapor is scanned and collected with an acid solution, the acid solution after being subjected to the scanning and collecting is changed to a concentrated and dried object on a substrate having a mirror surface, the concentrated and dried object is changed to a particle-like concentrated object using an acid, and the particle-like concentrated object is analyzed using a total reflection X-ray fluorescence analysis device.

13 Claims, 6 Drawing Sheets

U.S. PATENT DOCUMENTS

2005/0196881 A1  9/2005  Shiramizu

FOREIGN PATENT DOCUMENTS

| DE | 10 2004 041 410 A1 | 5/2005 |
|---|---|---|
| DE | 10 2005 008 068 A1 | 10/2005 |
| JP | 7-229864 | 8/1995 |
| JP | 2604037 | 1/1997 |
| JP | 10-307087 | 11/1998 |
| JP | 11-281542 | 10/1999 |
| JP | 2001-153768 | 6/2001 |
| JP | 3249316 | 11/2001 |
| JP | 2003-90809 | 3/2003 |
| JP | 2004-28787 | 1/2004 |

OTHER PUBLICATIONS

Matsumura, et al., QTAT Monitoring in ULSI Manufacturing Line by VPD-TXRF, Proc. of ISSM2002, pp. 43-46, (2002).

Official Action issued by the German Patent Office on Oct. 4, 1006, for German Patent Application No. 10 2005 023 872.6-52, and English-language translation thereof.

Notification of Reason for Rejection issued by the Japanese Patent Office on May 16, 2008, for Japanese Patent Application No. 2004-177270, and English-language translation thereof.

Yamagami et al., "Analysis of light elements on Si wafer by vapor-phase decomposition/total reflection X-ray fluorescence," The Japan Society for Analytical Chemistry (1999), 48:1005-11.

* cited by examiner

TOTAL REFLECTION X-RAY FLUORESCENCE ANALYSIS METHOD

CROSS-REFERENCE TO RELATED APPLICATION

This application is based upon and claims the benefit of priority from prior Japanese Patent Application No. 2004-177270 filed on Jun. 15, 2004 in Japan, the entire contents of which are incorporated herein by reference.

BACKGROUND OF THE INVENTION

1. Field of the Invention

The present invention relates to a total reflection X-ray fluorescence analysis method. Specifically, the present invention is used for a high-sensitivity total reflection X-ray fluorescence analysis.

2. Background Art

In total reflection X-ray fluorescence analysis, excited X-rays are made incident on the surface of a subject, under a total reflection condition, and X-ray fluorescence emitted from an impurity in the surface of the subject is detected by a semiconductor detector provided above the subject, thereby analyzing a very small amount of impurity element on the surface of a semiconductor substrate with a high sensitivity, and minimizing the scattering of excited X-rays and the influences of X-ray fluorescence emitted from the subject bulk.

In order to analyze impurities on a surface of a semiconductor substrate with a high sensitivity, a chemical analysis methods such as WSA (Wafer Surface Analysis) or VPD (Vapor Phase Decomposition) is also widely used. In WSA, a surface of a semiconductor substrate is exposed to an acid vapor to dissolve an oxide layer, and the surface of the substrate is scanned with a small amount of an acid solution to take impurities on the surface and the oxide layer in the solution. The impurity concentration in the solution is measured using Atomic Absorption Spectrometry (AAS), Inductively Coupled Plasma Mass Spectroscopy (ICP-MS), etc. to analyze impurities on the substrate surface.

Recently, an ultra high-sensitivity impurity analysis method as disclosed in Japanese Patent Nos. 2,604,037 and 3,249,316 has become available, in which total reflection X-ray fluorescence analysis and WSA are combined. In such a method, a solution containing an impurity is dried on a mirror substrate, and the dried residue is measured using total reflection X-ray fluorescence analysis. Using this ultra high-sensitivity impurity analysis method, it is possible to perform an ultra high-sensitivity analysis, which is comparable to WSA employing ICP-MS, without any special skill or experience.

However, when the technique disclosed in Japanese Patent No. 2,604,037 is used, it is necessary to concentrate and dry an impurity collecting solution so as to be in a range detectable by a semiconductor detector under conditions satisfying the total reflection condition. In addition, the sensitivity tends to be lowered due to the influences of the absorption and the scattering of X-ray fluorescence caused by the silicon matrix contained in the collecting solution. Accordingly, at present, the subjects that can be measured using this technique are very limited. When the technique disclosed in Japanese Patent No. 3,249,316 is used, there are problems in that when only the acid vapor exposure is performed as a pretreatment before performing a total reflection X-ray fluorescence analysis, the pretreatment is highly dependent on the surface condition of the substrate, thereby varying the measurement result, and that since the analysis area is small, the sensitivity is degraded by one to two orders as compared to a case where the scanning and the collecting are performed using the acid solution after the exposure.

SUMMARY OF THE INVENTION

A total reflection X-ray fluorescence analysis method according to an aspect of the present invention includes: exposing a semiconductor substrate to an acid vapor; scanning and collecting an impurity on a surface of the semiconductor substrate exposed to the acid vapor with an acid solution; concentrating and drying the acid solution used in the scanning and collecting on a substrate having a mirror surface to change the acid solution to a concentrated and dried object; changing the concentrated and dried object to a particle-like concentrated object using an acid; and analyzing the particle-like concentrated object using a total reflection X-ray fluorescence analysis device.

DESCRIPTION OF THE EMBODIMENTS

First Embodiment

Figure 4:
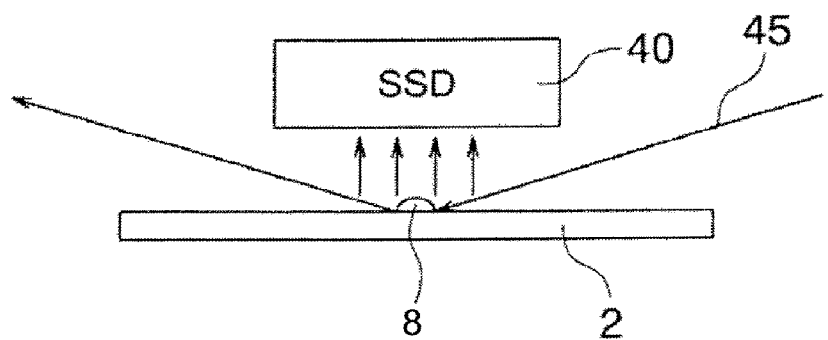
FIG. 4 shows an analysis step in a total reflection X-ray fluorescence analysis method according to the first embodiment of the present invention.
Figure 5:
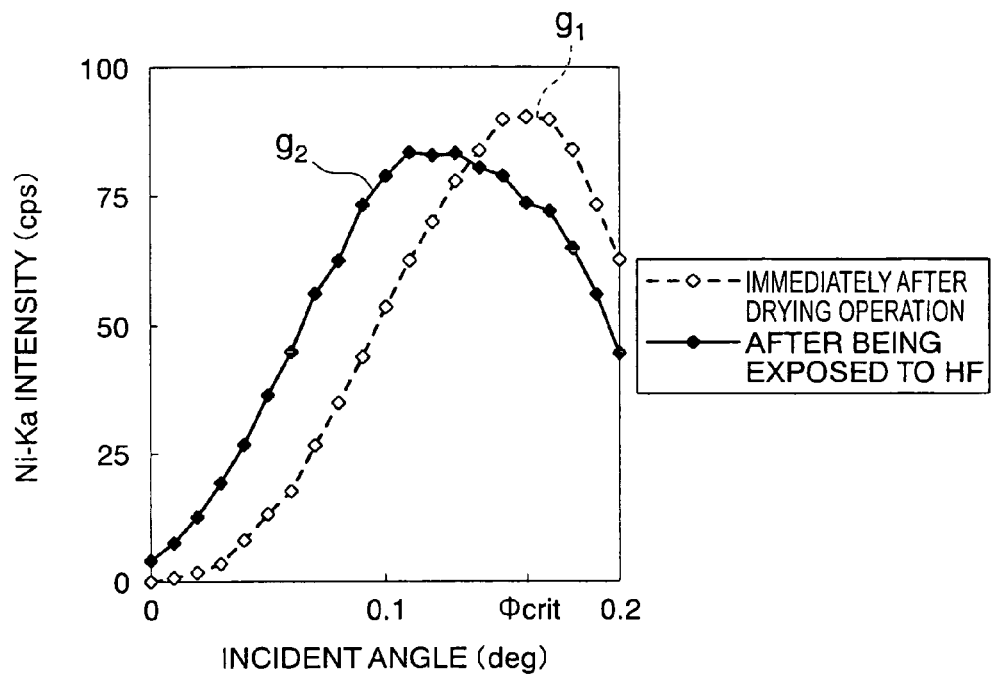
FIG. 5 is a graph showing the dependence of characteristic X-ray on incident angle, the characteristic X-ray being of an impurity contained in a dried residue in the first embodiment.
Figure 6:
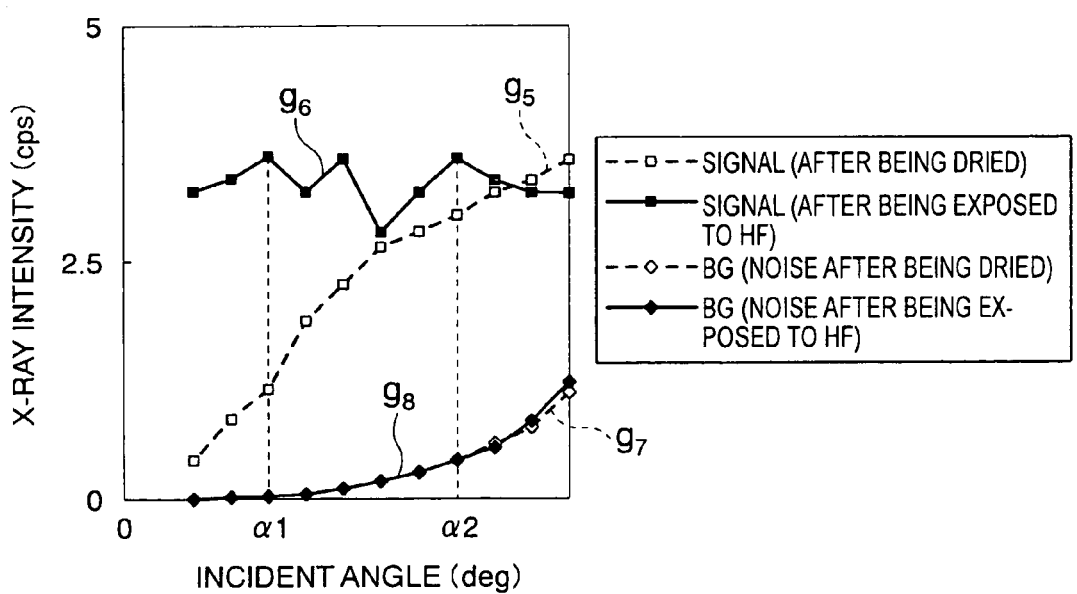
FIG. 6 is a graph showing the dependence of characteristic X-ray on incident angle, the characteristic X-ray being of an impurity contained in a dried residue of the first embodiment.
Figure 7:
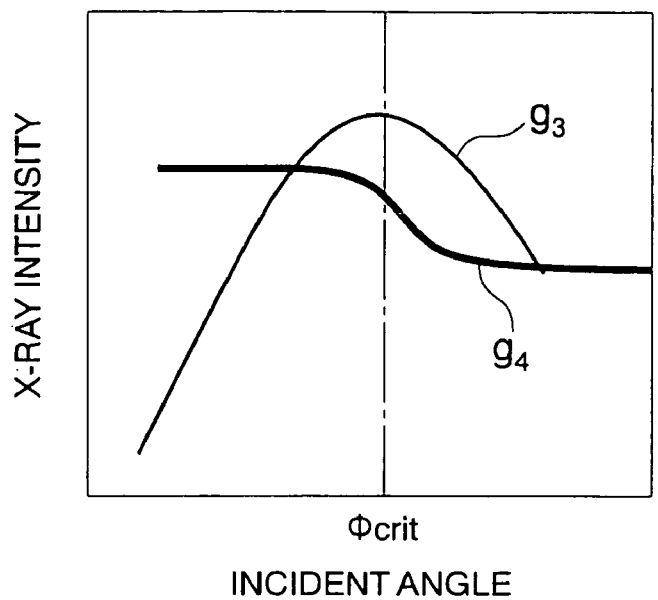
FIG. 7 is a graph showing the dependence of characteristic X-ray on incident angle in cases each having a different impurity adhesion state.

A total reflection X-ray fluorescence analysis method according to a first embodiment of the present invention will be described below with reference to FIGS. 1A to 7. FIGS. 1A to 4 schematically show analysis steps of the total reflection X-ray fluorescence analysis method of this embodiment. FIGS. 5 and 6 are graphs showing the dependence of characteristic X-ray of impurities contained in the dried residues on incident angle. FIG. 7 is a graph showing the dependence of characteristic X-ray on incident angle when the adhesion state is changed.

Figure 1A:
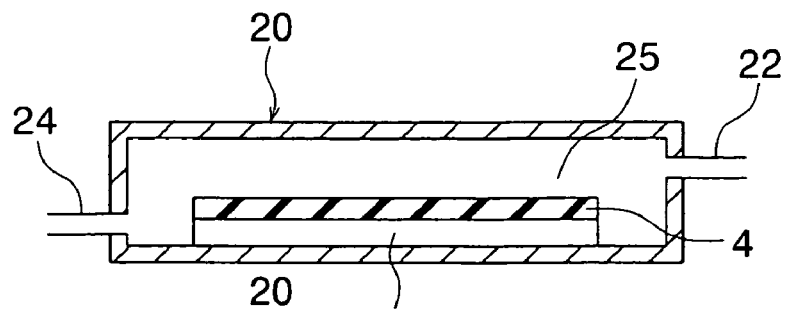
FIGS. 1A and 1B show analysis steps in a total reflection X-ray fluorescence analysis method according to a first embodiment of the present invention.
Figure 1B:
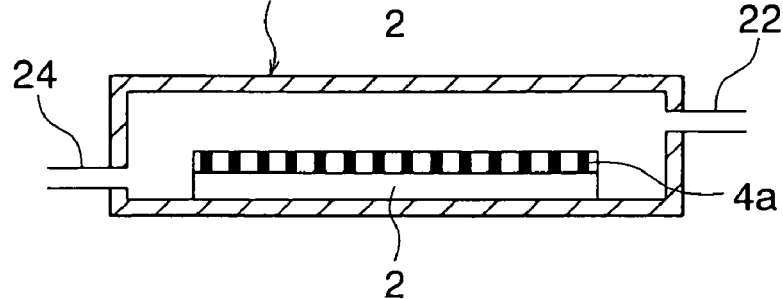

First, as shown in FIG. 1A, a semiconductor substrate 2, on which a native oxide layer 4 is formed, is placed within an airtight container of fluorine-containing resin 20. Then, HF gas 25 is introduced into the airtight container of fluorine-containing resin 20 from an inlet pipe 22, thereby exposing a surface of the semiconductor substrate 2 to an HF gas atmosphere for one hour. In this case, HF gas is always flowing through the airtight container of fluorine-containing resin 20, and is discharged from an outlet pipe 24. By exposing the surface of the semiconductor substrate 2 to the HF gas atmosphere for one hour, the native oxide layer on the semiconductor substrate 2 is dissolved to form a dissolved native oxide layer 4a, as shown in FIG. 1B.

Figure 2A:
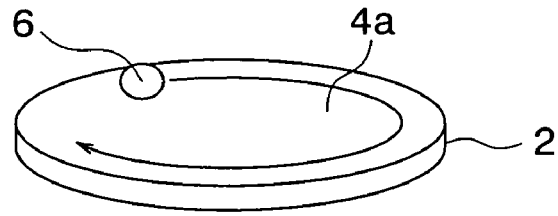
FIGS. 2A to 2C show analysis steps in the total reflection X-ray fluorescence analysis method according to the first embodiment of the present invention.
Figure 2B:
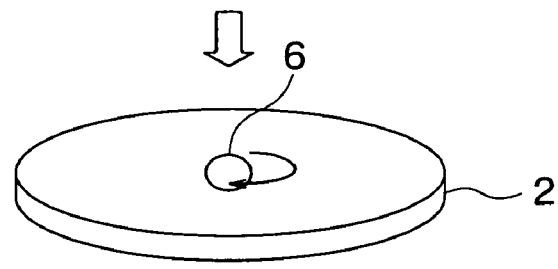
Figure 2C:
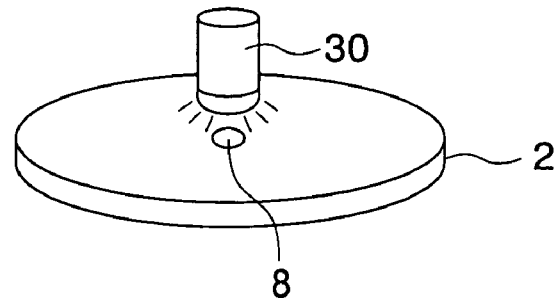

Next, the semiconductor substrate 2 with the dissolved native oxide layer 4a is taken out of the airtight container of fluorine-containing resin 20. Thereafter, a collecting solution of 200 µL containing 2% by weight in concentration of HF and 2% by weight in concentration of $H_2O_2$ is dropped on the semiconductor substrate 2, thereby forming a collection droplet 6 on the semiconductor substrate 2, as shown in FIG. 2A. The surface of the semiconductor substrate 2 is scanned with the collection droplet 6 to take impurities on the surface of the semiconductor substrate 2 and in the native oxide layer 4a in the collection droplet 6, as shown in FIG. 2B. After the scanning is completed, the collection droplet 6 is irradiated by an infrared lamp 30 to heat and dry the collection droplet 6 on the semiconductor substrate 2 to form a dried residue 8, as shown in FIG. 2C.

Figure 3:
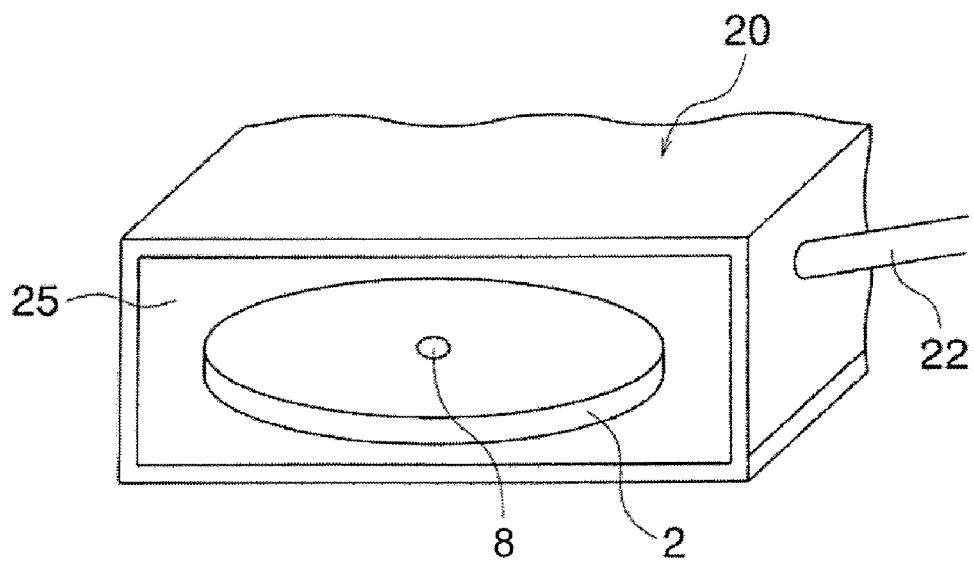
FIG. 3 shows an analysis step in the total reflection X-ray fluorescence analysis method according to the first embodiment of the present invention.

Then, as shown in FIG. 3, the semiconductor substrate 2, on which the dried residue 8 is formed, is placed within the airtight container 20 again, and HF gas 25 is guided thereto to expose the semiconductor substrate 2 to an HF gas atmosphere for 10 minutes. Subsequently, as shown in FIG. 4, the dried residue 8 is irradiated with total reflection X-ray 45 to measure an impurity concentration of the dried residue 8 using a total reflection X-ray fluorescence analysis device 40.

In FIG. 5, a characteristic curve $g_1$ shows the dependence of the Ni-Ka intensity on the incident angle, Ni-Ka being contained in the dried residue 8 after being subjected to the heating and drying operation using the infrared lamp 30. The X-ray intensity is lower at the smaller incident angle side, and rapidly increases around the critical angle φcrit. This means that the shape of adhering Ni is a plate shape, as can be understood from the characteristic curves $g_3$ and $g_4$ in FIG. 7. In FIG. 7, the characteristic curve $g_3$ shows the dependence of the characteristic X-ray on the incident angle when an impurity in a plate shape adheres to the semiconductor substrate 2, and the characteristic curve $g_4$ shows the dependence of the characteristic X-ray on the incident angle when an impurity in a particle shape adheres to the semiconductor substrate 2. When the shape of adhering impurity is a plate shape, the X-ray intensity becomes a maximum around the critical angle φcrit of the incident angle, as represented by the characteristic curve $g_3$, and when the shape is a particle shape, the X-ray intensity gradually decreases as the incident angel increases, except for the critical angle φcrit, around which the X-ray intensity rapidly decreases as the incident angel increases, as represented by the characteristic curve $g_4$.

The characteristic curve $g_2$ of FIG. 5 shows the dependence of Ni-Ka intensity on the incident angle after the dried residue 8 is exposed to the HF gas atmosphere. The peak of the characteristic curve $g_2$ is shifted to the lower incident angle side as compared to the characteristic curve $g_1$ where the dried residue 8 is dried, and the Ni-Ka intensity value of the peak is also lower. This means that the shape of adhering Ni is close to a particle shape represented by the characteristic curve $g_4$ shown in FIG. 7.

Similarly, FIG. 6 shows the characteristics of the dependence of Na on the incident angle. The characteristic curve $g_5$ of FIG. 6 represents the dependence of the Na intensity on the incident angle, Na being contained in the dried residue 8 after being dried by the infrared lamp 30. The characteristic curve $g_7$ represents the noise (background X-ray intensity) at this time. The characteristic curve $g_6$ represents the dependence of the Na intensity on the incident angle after the substrate is exposed to the HF gas atmosphere, and the characteristic curve $g_8$ represents the noise (background X-ray intensity) at this time. It can be clearly understood from the characteristic curves $g_5$ and $g_6$ of FIG. 6 that after being exposed to HF gas, the shape of the impurity adhering to the substrate is changed to a particle shape.

There are the following two advantages in the particle shape of impurities adhering to the substrate.
1) Since the analysis accuracy is improved, the dependence of the characteristic X-ray intensity on incident angle is decreased, so that the fluctuations in a measurement system do not considerably vary the X-ray incident angle.
2) Since the S/N ratio is improved, the analysis sensitivity can be improved.

In a total reflection X-ray fluorescence analysis, the less the incident angle is when an X-ray is made incident, the more the noise is reduced and the analysis sensitivity is improved. When calculated using data gathered after the substrate is subjected to the drying operation represented by the characteristic curve $g_5$ of FIG. 6, the S/N ratios of the incident angle α1 and the incident angle α2 are 25 and 7, respectively. Thus, with the lower incident angle (incident angle=α1), the sensitivity is improved by one order. However, when a lower incident angle is selected, there is a disadvantage that the signal intensity is also decreased. When the shape of the impurity adhering is a particle shape, the signal intensity at a lower incident angle is increased. By exposing the substrate to an HF gas, thereby optimizing the shape of the impurity adhering, it is possible to significantly improve the S/N ratio to 87 (when the incident angle is α1 in FIG. 6).

As described above, according to this embodiment, by exposing the dried residue to HF gas, it is possible to change the shape of impurity adhering to the semiconductor substrate to a particle shape, thereby improving the S/N ratio when an X-ray is made incident at a lower incident angle. Since the improvement in S/N ratio is not dependent on the kind of the specimen and the surface condition of the specimen, it is possible to achieve a total reflection X-ray fluorescence analysis method with a high sensitivity.

Although the semiconductor substrate is exposed to an HF gas atmosphere for one hour in this embodiment, of course the exposure time is determined by the kind and the thickness of a thin film formed on the surface of the substrate.

Furthermore, although the collecting solution contains HF (hydrofluoric acid) and hydrogen peroxide solution in this embodiment, the collecting solution may contain at least one substance selected from hydrofluoric acid, nitric acid, hydrochloric acid, hydrogen peroxide solution, sulfuric acid, phosphoric acid, and ozone.

Moreover, although the dried residue is exposed to the HF gas atmosphere once in this embodiment, it is possible to expose it two or more times.

Furthermore, although HF gas (hydrofluoric acid gas) is used as the atmosphere to which the dried residue is exposed in this embodiment, with an acid vapor containing, e.g., at least one substance selected from nitric acid, hydrochloric acid, hydrogen peroxide solution, sulfuric acid, phosphoric acid, and ozone, the same effect can be obtained.

Moreover, although the drying operation and the HF gas exposure operation are performed after the scanning and collecting operation in this embodiment, it is possible to add an acid solution after the drying operation, and to perform another drying operation. The acid solution adding operation and the drying operation can be repeated several times. By repeating the adding and the drying of an acid solution, it is possible to remove the matrix element such as silicon to curb the scattering of X-rays due to such a matrix, thereby improving the analysis sensitivity and enabling a highly accurate measurement. In this case, the acid solution can contain at least a substance selected from hydrofluoric acid, nitric acid, hydrochloric acid, hydrogen peroxide solution, sulfuric acid, phosphoric acid, and ozone.

Furthermore, although HF gas always flows in this embodiment, as long as the semiconductor substrate is exposed to HF gas, the container can be made airtight after HF gas is introduced therein.

In addition, although the collecting solution is dropped on the substrate to be analyzed, the collection droplet is scanned, and thereafter the collection droplet is dried in this embodiment, it is possible to perform the drying operation, the HF gas atmosphere exposure operation, and the total reflection X-ray fluorescence analysis operation on another substrate having a mirror surface. In this case, a plurality of collection droplets can be dried on the same substrate at a time, thereby improving the analysis throughput considerably.

Second Embodiment

Figure 12:
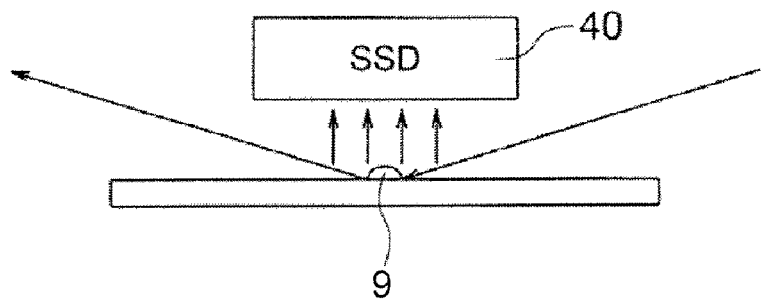
FIG. 12 shows an analysis step in the total reflection X-ray fluorescence analysis method according to the second embodiment of the present invention.
Figure 13A:
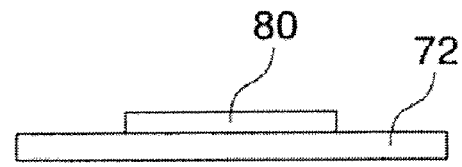
FIGS. 13A to 13C schematically explain the dried residue adhesion state in the second embodiment.
Figure 13B:
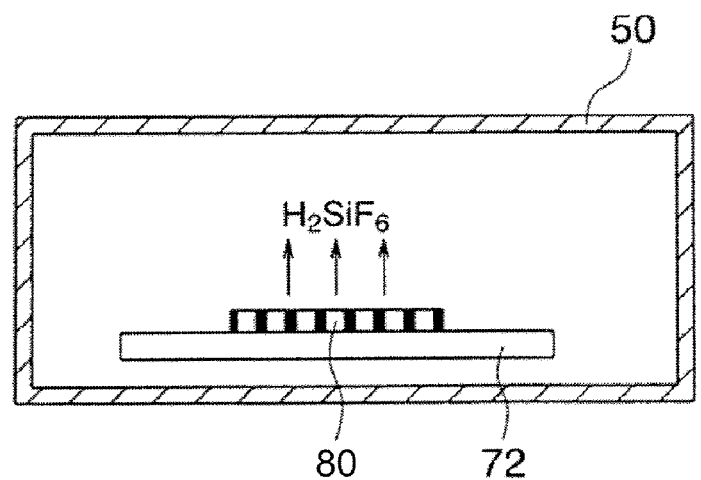
Figure 13C:
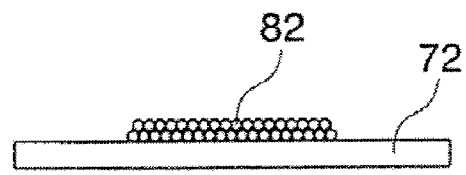

Next, a total reflection X-ray fluorescence analysis method according to a second embodiment of the present invention will be described below with reference to FIGS. 8A to 13C. FIGS. 8A to 12 schematically show the analysis steps of the total reflection X-ray fluorescence analysis method according to this embodiment. FIGS. 13A to 13B schematically explain the state of the dried residue adhering to the substrate.

Figure 8A:
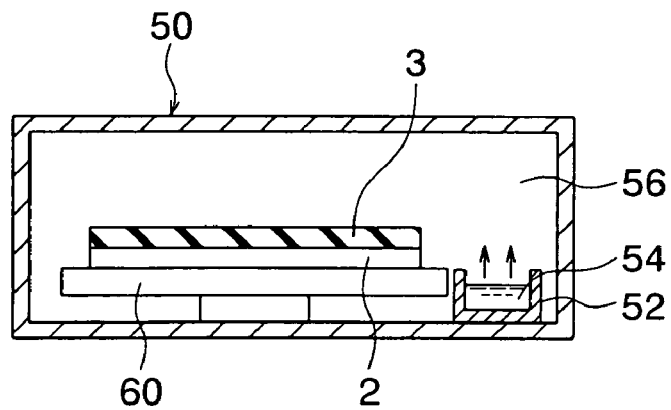
FIGS. 8A and 8B show analysis steps in a total reflection X-ray fluorescence analysis method according to a second embodiment of the present invention.
Figure 8B:
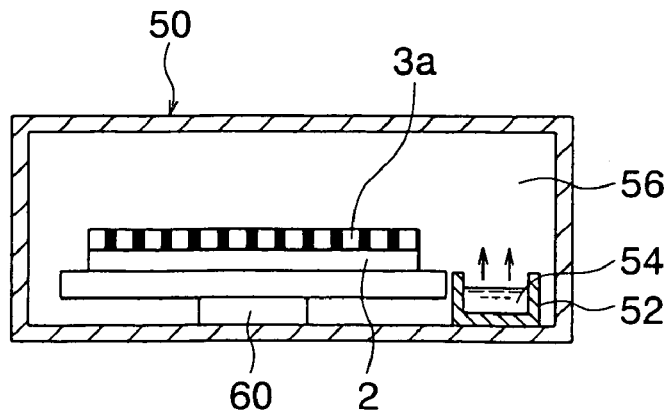

First, as shown in FIGS. 8A and 8B, a semiconductor substrate 2, on which an oxynitride layer 3 is formed, and a container 52 containing an HF solution 54 are placed within an airtight container of fluorine-containing resin 50 for one hour to expose the oxynitride layer 3 on the surface of the semiconductor substrate 2 to an atmosphere of HF gas 56 generated from the container 52, thereby dissolving the oxynitride layer 3 to form a dissolved oxynitride layer 3a. In this case, the semiconductor substrate 2 is placed on a platform 60 within the airtight container of fluorine-containing resin 50.

Figure 9A:
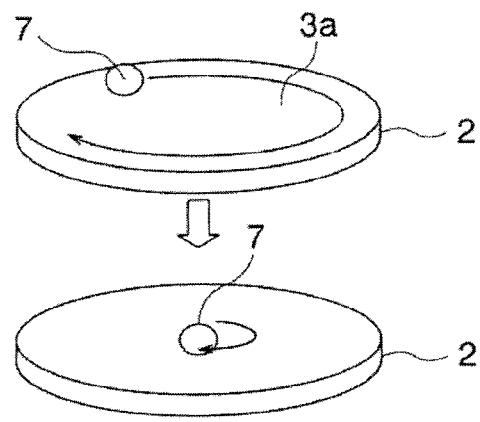
FIGS. 9A and 9B show analysis steps in the total reflection X-ray fluorescence analysis method according to the second embodiment of the present invention.
Figure 9B:

Next, the semiconductor substrate 2 with the oxynitride layer 3 being dissolved is taken out of the airtight container of fluorine-containing resin 50. Thereafter, a collecting solution of 100 µL containing 2% by weight in concentration of HF and 2% by weight in concentration of $H_2O_2$ is dropped on the semiconductor substrate 2, thereby forming a collection droplet 7 on the semiconductor substrate 2, as shown in FIG. 9A. The surface of the semiconductor substrate 2 is scanned with the collection droplet 7 to take in the collection droplet 7 impurities on the surface of the semiconductor substrate 2 and in the oxynitride layer 3, as shown in FIG. 9B.

Figure 10:
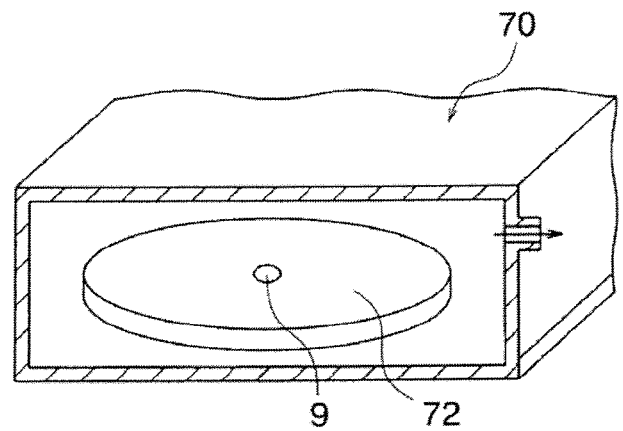
FIG. 10 shows an analysis step in the total reflection X-ray fluorescence analysis method according to the second embodiment of the present invention.

After the scanning and collecting operation is completed, the collection droplet 7 containing an impurity is moved onto an analysis amorphous substrate 72, which has been mirror-processed, as shown in FIG. 10. The amorphous substrate 72 is placed within a reduced-pressure drying device 70, thereby drying the collection droplet 7 with a reduced pressure. Thus, the collection droplet 7 becomes a dried residue 9.

Figure 11:
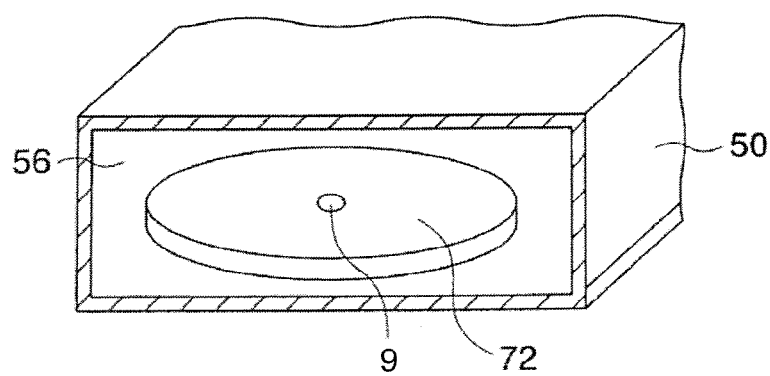
FIG. 11 shows an analysis step in the total reflection X-ray fluorescence analysis method according to the second embodiment of the present invention.

After the drying operation, the amorphous substrate 72 with the dried residue 9 is put into the airtight container 50 again to expose it to an HF gas atmosphere 56 for 10 minutes, as shown in FIG. 11. Thereafter, as shown in FIG. 12, the impurity concentration of the dried residue 9 is measured with a total reflection X-ray fluorescence analysis device 40.

Unlike this embodiment, if the total reflection X-ray fluorescence analysis is performed after the reduced-pressure drying operation, it is not possible to perform the measurement operation due to a great degree of scattering caused by the dried residue. However, if a total reflection X-ray fluorescence analysis is performed after the exposing of the dried residue to an HF gas atmosphere as in the case of this embodiment, the scattering is decreased, thereby enabling a total reflection X-ray fluorescence analysis. The reason for this may be that the silicon matrix that has not been completely removed at the time of the reduced-pressure drying operation is diffused as silicon fluoride when the substrate is exposed to the HF gas atmosphere again. This will be described below with reference to FIGS. 13A, 13B, and 13C. As shown in FIG. 13A, when a substrate 72, to which a dried residue 80 in a plate shape adheres, is exposed to the HF gas atmosphere in the airtight container 50, the silicon matrix contained in the dried residue 80 is diffused as silicon fluoride as shown in FIG. 13B, thereby forming impurity particles 82 adhering to the substrate 72. When exposed to the HF gas atmosphere shown in FIG. 8B, silicon matrix is also diffused as silicon fluoride.

In this embodiment, the solution having collected an impurity is dried and exposed to an acid vapor, thereby changing the state of the impurity contained in the dried residue from a film state to a particle state without being dependent on the state of the specimen. Furthermore, a large amount of the silicon matrix contained in the collecting solution is removed by two stages. Accordingly, the characteristic X-ray intensity at the lower incident angle side increases, and the scattering of the excited X-rays due to the silicon matrix and the X-ray fluorescence absorption of impurity elements, in particular light elements such as Na can be curbed.

By using the total reflection X-ray fluorescence analysis according to this embodiment, it is possible to obtain a high S/N (signal/noise) ratio without being dependent on the surface condition. Accordingly, it is possible to perform a total reflection X-ray fluorescence analysis on various specimens with a high sensitivity.

Although the semiconductor substrate is exposed to an HF gas atmosphere for one hour in this embodiment, of course the exposure time is determined by the kind and the thickness of a thin film formed on the surface of the substrate.

Furthermore, although the collecting solution contains HF (hydrofluoric acid) and hydrogen peroxide solution in this embodiment, the collecting solution may include at least one substance selected from hydrofluoric acid, nitric acid, hydrochloric acid, hydrogen peroxide solution, sulfuric acid, phosphoric acid, and ozone.

Moreover, although the dried residue is exposed to the HF gas atmosphere once in this embodiment, it is possible to expose it two or more times.

Furthermore, although HF gas (hydrofluoric acid gas) is used as the atmosphere to which the dried residue is exposed in this embodiment, with an acid vapor containing, e.g., at least one substance selected from nitric acid, hydrochloric acid, hydrogen peroxide solution, sulfuric acid, phosphoric acid, and ozone, the same effect can be obtained.

Moreover, although the drying operation and the HF gas exposure operation are performed after the scanning and collecting operation in this embodiment, it is possible to add an acid solution after the drying operation, and to perform another drying operation. The acid solution adding operation and the drying operation can be repeated for several times. By repeating the adding and the drying of an acid solution, it is possible to remove the matrix element such as silicon to curb the scattering of X-rays due to such a matrix, thereby improving the analysis sensitivity and enabling a highly accurate measurement. In this case, the acid solution can contain at least a substance selected from hydrofluoric acid, nitric acid, hydrochloric acid, hydrogen peroxide solution, sulfuric acid, phosphoric acid, and ozone.

In this embodiment, the drying operation, the HF gas atmosphere exposure operation, and the total reflection X-ray fluorescence analysis operation are performed on an amorphous substrate having a mirror-state surface. Accordingly, it is possible to dry a plurality of collection droplets on one substrate, thereby improving the throughput considerably.

Although the collection droplet is dried with heat in the first embodiment and is dried under a reduced pressure in the second embodiment, the drying with heat and the drying under a reduced pressure can be combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concepts as defined by the appended claims and their equivalents.

The invention claimed is:

1. A total reflection X-ray fluorescence analysis method comprising:
   exposing a semiconductor substrate to a first acid vapor;
   scanning and collecting an impurity on a surface of the semiconductor substrate exposed to the acid vapor with an acid solution;
   moving the acid solution used in the scanning and collecting to a substrate having a mirror surface;
   concentrating and drying the acid solution on the substrate to change the acid solution to a concentrated and dried object;
   exposing the concentrated and dried object to a second acid vapor to transform the concentrated and dried object to a particle-like concentrated object; and
   analyzing the particle-like concentrated object using a total reflection X-ray fluorescence analysis device.

2. The total reflection X-ray fluorescence analysis method according to claim 1, wherein the acid used to change the concentrated and dried object to the particle-like concentrated object contains at least one substance selected from the group consisting of hydrofluoric acid, nitric acid, hydrochloric acid, hydrogen peroxide solution, sulfuric acid, phosphoric acid, and ozone.

3. The total reflection X-ray fluorescence analysis method according to claim 2, wherein the acid solution used to scan and collect the impurity on the surface of the semiconductor substrate contains at least one substance selected from the group consisting of hydrofluoric acid, nitric acid, hydrochloric acid, hydrogen peroxide solution, sulfuric acid, phosphoric acid, and ozone.

4. The total reflection X-ray fluorescence analysis method according to claim 2, wherein a layer is formed on the surface of the semiconductor substrate before being exposed to the first acid vapor.

5. The total reflection X-ray fluorescence analysis method according to claim 2, wherein the acid solution is changed to the concentrated and dried object using a drying method selected from a heat drying method, a reduced-pressure drying method, and a reduced-pressure heat drying method performed on the acid solution used in the scanning and collecting.

6. The total reflection X-ray fluorescence analysis method according to claim 1, wherein the acid solution used to scan and collect the impurity on the surface of the semiconductor substrate contains at least one substance selected from the group consisting of hydrofluoric acid, nitric acid, hydrochloric acid, hydrogen peroxide solution, sulfuric acid, phosphoric acid, and ozone.

7. The total reflection X-ray fluorescence analysis method according to claim 6, wherein a layer is formed on the surface of the semiconductor substrate before being exposed to the first acid vapor.

8. The total reflection X-ray fluorescence analysis method according to claim 6, wherein the acid solution is changed to the concentrated and dried object using a drying method selected from a heat drying method, a reduced-pressure drying method, and a reduced-pressure heat drying method performed on the acid solution used in the scanning and collecting.

9. The total reflection X-ray fluorescence analysis method according to claim 1, wherein a layer is formed on the surface of the semiconductor substrate before being exposed to the first acid vapor.

10. The total reflection X-ray fluorescence analysis method according to claim 9, wherein the acid solution is changed to the concentrated and dried object using a drying method selected from a heat drying method, a reduced-pressure drying method, and a reduced-pressure heat drying method performed on the acid solution used in the scanning and collecting.

11. The total reflection X-ray fluorescence analysis method according to claim 1, wherein the acid solution is changed to the concentrated and dried object using a drying method selected from a heat drying method, a reduced-pressure drying method, and a reduced-pressure heat drying method performed on the acid solution used in the scanning and collecting.

12. The total reflection X-ray fluorescence analysis method according to claim 1, wherein after the acid solution is changed to the concentrated and dried object, adding of acid solution and drying of acid solution thereafter are performed at least one time each.

13. The total reflection X-ray fluorescence analysis method according to claim 1, wherein the semiconductor substrate used in the scanning and collecting is different from the substrate having a mirror surface.

* * * * *